(12) United States Patent
Becker et al.

(10) Patent No.: US 9,067,876 B2
(45) Date of Patent: Jun. 30, 2015

(54) HYDROFORMYLATION PROCESS

(71) Applicant: Dow Technology Investments LLC, Midland, MI (US)

(72) Inventors: Michael C. Becker, Dickinson, TX (US); James D. Duston, Alvin, TX (US); Victoria L. Biedenstein, Eden Prairie, MN (US); Steven H. Fisher, Houston, TX (US); Glenn A. Miller, South Charleston, WV (US)

(73) Assignee: Dow Technology Investments LLC

( * ) Notice: Subject to any disclaimer, the term of this patent is extended or adjusted under 35 U.S.C. 154(b) by 0 days.

(21) Appl. No.: 14/366,033

(22) PCT Filed: Oct. 24, 2012

(86) PCT No.: PCT/US2012/061511
§ 371 (c)(1),
(2) Date: Jun. 17, 2014

(87) PCT Pub. No.: WO2013/095766
PCT Pub. Date: Jun. 27, 2013

(65) Prior Publication Data
US 2014/0350305 A1 Nov. 27, 2014

Related U.S. Application Data

(60) Provisional application No. 61/577,708, filed on Dec. 20, 2011.

(51) Int. Cl.
*C07C 45/50* (2006.01)
*B01J 19/00* (2006.01)
*B01J 19/18* (2006.01)

(52) U.S. Cl.
CPC .............. *C07C 45/50* (2013.01); *B01J 19/0013* (2013.01); *B01J 19/006* (2013.01); *B01J 19/1862* (2013.01); *B01J 2219/00083* (2013.01); *B01J 2219/00108* (2013.01); *B01J 2219/0011* (2013.01)

(58) Field of Classification Search
CPC ....................................................... C07C 45/50
USPC .......................................................... 568/454
See application file for complete search history.

(56) References Cited

U.S. PATENT DOCUMENTS

| | | | |
|---|---|---|---|
| 3,094,564 A * | 6/1963 | Mertzweiller et al. ........ | 568/452 |
| 3,527,809 A | 9/1970 | Pruett et al. | |
| 4,148,830 A | 4/1979 | Pruett et al. | |
| 4,247,486 A * | 1/1981 | Brewester et al. ............ | 568/454 |
| 4,283,562 A | 8/1981 | Billig et al. | |
| 4,298,541 A | 11/1981 | Oswald et al. | |
| 4,302,401 A | 11/1981 | Oswald | |
| 4,400,548 A | 8/1983 | Abatjoglou et al. | |
| 4,482,749 A | 11/1984 | Dennis et al. | |
| 4,496,768 A | 1/1985 | Dennis et al. | |
| 4,496,769 A | 1/1985 | Dennis et al. | |
| 4,593,127 A | 6/1986 | Bunning et al. | |
| 4,599,206 A | 7/1986 | Billig et al. | |
| 4,668,651 A | 5/1987 | Billig et al. | |
| 5,001,274 A | 3/1991 | Bunning | |
| 5,105,018 A * | 4/1992 | Miyazawa et al. ............ | 568/453 |
| 5,288,918 A | 2/1994 | Maher et al. | |
| 5,367,106 A | 11/1994 | Unruh et al. | |
| 5,744,650 A | 4/1998 | Nicholson et al. | |
| 5,932,772 A | 8/1999 | Argyropoulos et al. | |
| 5,952,530 A | 9/1999 | Argyropoulos et al. | |
| 7,405,329 B2 | 7/2008 | Beadle et al. | |
| 7,550,406 B2 | 6/2009 | Jeon et al. | |
| 2007/0282132 A1 * | 12/2007 | Beadle et al. ................. | 568/451 |
| 2008/0251456 A1 | 10/2008 | Wiese et al. | |

FOREIGN PATENT DOCUMENTS

GB 1338237 11/1973
WO 2010081526 7/2010

OTHER PUBLICATIONS

"Low-pressure OXO process yields a better product mix", Chemical Engineering, Dec. 5, 1977, pp. 110-115.
C.W. Kohlpaintner, R.W. Fischer, B. Cornils; "Aqueous biphasic catalysis: Ruhrchemie/Rhone-Poulenc oxo process", Applied Catalysis A: General, 221, 2001, pp. 219-225.

* cited by examiner

*Primary Examiner* — Sikarl Witherspoon (57) ABSTRACT

Disclosed is an improved exothermic hydroformylation process having at least two reaction stages. Cooling is provided by externally cooling a stream of reaction mixture from one of the stages, dividing the cooled stream into at least two cooled reaction mixture streams; transferring one cooled reaction mixture stream back into the same reaction stage from which it was removed to cool the reaction mixture in that reaction stage; and transferring at least one cooled reaction mixture stream(s) into and through heat exchange means that cool a different reaction stage, and returning it to the same reaction stage from which it was removed.

15 Claims, 2 Drawing Sheets

HYDROFORMYLATION PROCESS

CROSS-REFERENCE TO RELATED APPLICATIONS

This application claims priority from provisional application Ser. No. 61/577,708, filed Dec. 20, 2011, which is incorporated herein by reference in its entirety.

FIELD OF THE INVENTION

The present invention relates to an improved method for cooling hydroformylation processes which include a catalyzed, exothermic reaction and have at least two reaction stages. In particular, it relates to a process for the hydroformylation of olefins to give aldehydes. Using the process according to the present invention, process temperature control is optimized and minimizes contamination of the reaction mixture, frequently containing expensive catalyst, from cooling medium leakages.

BACKGROUND

Hydroformylation is a well known reaction in which an olefin is reacted under suitable temperature and pressure conditions with hydrogen and carbon monoxide in the presence of a hydroformylation catalyst to give an aldehyde, or a mixture of aldehydes, having one more carbon atoms than the starting olefin. For example, a hydroformylation reaction with propylene will yield a mixture of n- and iso-butyraldehydes, of which the straight chain n-isomer is usually the more commercially desirable material. The hydrogen and carbon monoxide will generally be supplied to the hydroformylation reactor as synthesis gas. Examples of hydroformylation processes can be found in U.S. Pat. Nos. 4,247,486, 4,482,749, 4,496,768, 4,496,769, 4,593,127, 4,599,206, 4,668,651, 5,001,274, 5,105,018, 5,367,106 which are incorporated herein by reference.

Cooling in these processes has generally involved (a) typical individual reactor cooling by known internal or external heat exchangers and/or (b) using an external heat exchanger on the process stream of reaction mixture flowing from a first reactor to a second reactor, including cooling with the return of a cooled stream to the original reactor. See FIG. 1. For example, in U.S. Pat. No. 4,247,486 it is taught that the catalyst-containing reaction streams or mixtures are desirably retained in the reactor (and sent to external cooling) to avoid losses.

Rhodium complex catalysts are now conventionally used in the reaction mixtures in the hydroformylation of olefins permitting lower operating pressures and yielding desirable aldehyde product ratios. Since the rhodium catalyst is non-volatile, product recovery and catalyst reuse is greatly simplified. See "Low-pressure OXO process yields a better product mix", Chemical Engineering, Dec. 5, 1977 and U.S. Pat. No. 3,527,809, GB-A-1338237 and GB-A-1582010 which are incorporated herein by reference. Since rhodium catalysts are so expensive, it is very desirable to utilize this highly expensive metal in the most economically effective way. The reaction solution for the hydroformylation reaction will generally also contain excess ligand which, in many cases, is also very expensive. Therefore, in any cooling of these reactions, catalyst and process fluid losses need to be avoided or minimized.

SUMMARY OF THE INVENTION

Therefore, issues with hydroformylation reaction cooling and catalyst effectiveness have been analyzed resulting in an improved process according to the present invention. In one aspect the present invention is an improved exothermic hydroformylation process having at least two reaction stages, comprising the following steps: (a) reacting hydroformylation reactants exothermically in a first reaction stage in a fluid reaction mixture to form a reaction product; (b) transferring a process stream of fluid reaction mixture from a reaction stage to one or more later and separate reaction stages(s) for further exothermic, product-forming reaction and then to a product recovery unit operation; (c) transferring a heat transfer stream of reaction mixture from a reaction stage to an external heat exchanger where it is cooled and dividing the cooled stream into multiple cooled reaction mixture streams; (d) transferring a cooled reaction mixture stream from step (c) back into the same reaction stage from which it was removed to cool the reaction mixture in that reaction stage; (e) transferring at least one cooled reaction mixture stream(s) from step (c) into and through heat exchange means that cool a different reaction stage, and returning it to the same reaction stage from which removed; and (f) separating and recovering a reaction product from the reaction mixture and optionally recycling at least some reaction mixture components to the reaction mixture in a reaction stage.

In other included alternative embodiments of this process, it is: comprising at least two reaction stages that are in separate reactor vessels or comprising at least two reaction stages that are in the same reactor vessel and separated by baffles. In other included alternative embodiments of this process, at least two different rhodium-containing hydroformylation catalysts are employed and are employed in different reaction stages and/or catalyst is recycled from step (f) back to the reaction mixture in a reaction stage.

In another included alternative embodiment of the above process, it is an improved hydroformylation process for producing an aldehyde or a mixture of aldehydes and having at least first and second separate reaction stages, comprising the following steps: (a) reacting hydroformylation reactants comprising an olefin, hydrogen and carbon monoxide exothermically in a liquid reaction mixture in a first reaction stage using a rhodium-containing hydroformylation catalyst to give an aldehyde or a mixture of aldehydes having one more carbon atom than the starting olefin; (b) transferring a process stream of reaction mixture from the first reaction stage to the second reaction stages(s) for further exothermic conversion of reactants into aldehyde product; (c) transferring a heat transfer stream of reaction mixture from the first reaction stage to an external cooling heat exchanger where it is cooled and dividing the cooled stream into two or more cooled reaction mixture streams; (d) transferring the first cooled reaction mixture stream from step (c) back into the first reaction stage from which it was removed to cool the reaction mixture in that reaction stage; and (e) transferring the remaining cooled reaction mixture stream(s) from step (c) into and through heat exchange means that cools subsequent reaction stage(s), and returning them to the first reaction stage.

In a further aspect of the above process, a rhodium-phosphorus complex catalyst and free phosphorus ligand are used. Another alternative embodiment of such process is where a product-containing gaseous product mixture is transferred out of a reaction stage to a catalyst removal means, from which catalyst removal means (a) catalyst is returned to the reaction stage and (b) the gaseous product reaction mixture stream (with unreacted reactants) is transferred to the second reaction stages(s) for further exothermic conversion of reactants into aldehyde product and a recycle stream containing gases is returned to the reaction mixture.

In another embodiment, the present invention is an improved hydroformylation process as generally described above but comprises using two agitated reactors, each having a single reaction stage, wherein the cooled mixture stream from the external cooling heat exchanger is divided into two cooled reaction mixture streams with one cooled stream returned to the first reaction stage and the second cooled stream provided to heat exchange means in the second reactor.

In another embodiment, the present invention is an improved hydroformylation process as generally described above but comprises using an agitated reactor vessel with at least two separate reaction stages separated by baffles wherein a stream of cooled reaction mixture from the external cooling heat exchanger is returned to the first reaction stage and streams of cooled reaction mixture from the external cooling heat exchanger are provided to heat exchange means in the other reaction stage(s), used to cool the reaction mixtures in those stages and then returned to the reaction mixture in the first reaction stage.

In another embodiment, the present invention is an improved hydroformylation process as generally described above but comprising using two agitated reactor vessels, the first having a single reaction stage, and the second having 2 or more stages separated by baffles, wherein the cooled reaction mixture stream from the external cooling heat exchanger is divided into multiple cooled reaction mixture streams with one cooled stream returned to the first reaction stage and the remainder of the cooled streams provided to some or all of the internal coil heat exchange means in the second reactor.

Other aspects of the invention include improved hydroformylation processes as generally described above where: (a) the olefin is selected from ethylene, propylene, 1-butene, 2-butene (cis or trans), isobutene and mixtures thereof; (b) the olefin is ethylene or propylene; (c) uncooled reaction mixture is added to the cooled reaction mixture from the external cooling heat exchanger to achieve a desired temperature in the cooled reaction mixture stream provided to the heat exchange means that cools a subsequent reaction stage; and/or (d) wherein the cooled mixture stream from the external cooling heat exchanger is provided to internal coil heat exchange means in the subsequent reaction stage(s).

DETAILED DESCRIPTION

In studying hydroformylation catalyst effectiveness generally, the primary concerns include contamination with poisons, such as for rhodium catalyst, sulfur, chloride or air which inactivate the catalyst. Another concern for rhodium catalyst is the presence of heavies promoters, generally Lewis acids or bases that catalyze the aldol or Cannizarro reaction of the aldehydes to make materials that are not readily removed from the system and eventually choke the system, necessitating a catalyst change.

Contaminants affecting effectiveness may arise from many sources but it has been found that heat exchanger coolant leakage into the catalyst solution is a consistent problem. Coolants often comprise process water with a wide variety of inactivating compounds which can leak into the catalyst solution including dissolved air, anti-scale additives (many are sulfur-based), rust (a potent heavies promoter), sodium chloride (especially if sea-water is used as the cooling medium), glycols, and the like. Minimizing the exposure of catalyst solutions to process equipment that may leak these contaminants into the catalyst solution will reduce the risk of catalyst deactivation or premature aging.

Since it is necessary to cost effectively cool hydroformylation and other exothermic reactions, it is not possible to eliminate all the equipment containing cooling medium. As shown in the drawings, in the prior art a single external heat exchanger has been used for providing cooled first stage reaction mixture into both first and second hydroformylation reaction stages. However, problems with using the cooled catalyst-containing reaction mixture from the first reactor to directly cool the second reactor include insufficient cooling for the second stage, detrimentally affecting reaction rates and balance in both reactors, and difficult process control. Plus, situations where catalysts based on different, incompatible ligands are employed in separate reactors preclude significant direct flow of the previous reaction mixture for cooling purposes. See for example, U.S. Pat. Nos. 7,550,406 and 4,496,768.

However, reducing the number of heat exchangers in service minimizes the maintenance and simplifies the surveillance of potential issues with routine maintenance activities. According to the present invention, therefore, an improved process is provided for using one externally located cooling heat exchanger to more effectively service at least two reaction stages rather than separate cooling heat exchangers for each. As would be typical, cooled reaction mixture stream from the heat exchanger is returned to the same reaction stage from which it was removed to cool the reaction mixture in that reaction stage while one or more other cooled reaction mixture stream(s) are supplied to and passed through heat exchange means for cooling one or more different reaction stage(s) and are returned to the same reaction stage from which it was originally removed. Although needing to be somewhat larger and accommodate a larger heat load, a single cooling heat exchanger is typically not multiplied in size nor expense corresponding exactly to separate heat exchangers that it may replace, especially since the heat load in later reactors in a multi-staged exothermic process is typically smaller than in the first reactor. The effort and expense savings in maintenance are clear.

In the improved process provided according to the present invention, the cooled reaction mixture from the external heat exchanger is used as heat exchange medium in the heat exchanger for a subsequent reaction stage without mixing into the contents of the subsequent reaction stages. In the case of any minor leakage of the fluids between the subsequent reaction stage and its heat exchanger, the fluids are essentially the same or at least very similar and will be recycled into the system without impact on catalyst activity, product losses, or process efficiency.

The diversion of some of the process fluid from the first reaction stage heat exchanger (after the heat exchanger) can be adjusted to avoid impact on the catalyst activity or fluid level in the first reaction stage thus maintaining good temperature control in the first reactor. Heat transfer in the subsequent reaction stage can be controlled by varying the flow of the fluid in the subsequent reaction stage heat exchanger (e.g., through a cooling coil or external jacket on the subsequent reaction stage). Optionally, the heat transfer in the subsequent reaction stage can also be controlled by varying the temperature of the fluid in the subsequent reaction stage heat exchanger. This is accomplished by simply mixing cooled reaction fluid with uncooled reaction fluid to achieve the desired inlet temperature to the heat exchanger in the subsequent reaction stage.

An additional advantage in the case of a hydroformylation process is related to maintaining a low difference between the process fluid temperature and the inlet coolant temperature to avoid cycling such as described in U.S. Pat. No. 5,744,650, incorporated herein by reference. The process fluid temperature from the first reactor heat exchanger will be similar to the outlet coolant temperature of the first reactor heat exchanger and can be controlled closer to the process fluid temperature of the subsequent reaction stages then with fresh coolant fluid such as, for example, river water in the winter. This feature helps keep a low difference between the process fluid temperature in the subsequent reaction stages and the inlet coolant temperature of its heat exchanger thus improving process control stability and reducing capital requirement for this process.

External Cooling Heat Exchangers

A critical feature for the practice of the present invention is the utilization of external cooling heat exchange means for cooling the reaction mixture, i.e., removing the heat generated in the exothermic reaction. In general, any of the various known types of external heat exchanger means can be used for receiving and externally cooling the removed reaction mixture stream. These are all generally well known and commercially available and include all the general types of external cooling heat exchangers that use cooling mediums of air, water (including tempered water, brine), non-aqueous heat exchange fluids or refrigerants. The types and models of suitable external cooling heat exchangers are well known and commercially available and include shell and tube, plate and frame, and the like, which can be operated as single or multiple pass, with closed or open cooling medium supply. These are taught, for example in Perry's Chemical Engineers' Handbook, 8th Edition which is specifically referred to and incorporated herein.

Pumps for the supply and removal of the reaction mixture are similarly well known and commercially available and include direct displacement and centrifugal style pumps. The type and design are not important for the present invention except that they must move sufficient material to affect sufficient flow through the heat exchangers to effect sufficient heat removal. They should also be designed to prevent contamination of the catalyst solution with pump oil, etc.

Reaction Stage Heat Exchange Means

In general, various known types of heat exchanger means can be used for receiving the initial cooled streams from the external cooling heat exchanger for use to remove heat from other specific reaction stages. These are all generally well known and commercially available and include the following general types of heat exchangers that can receive the cooled reaction mixture from the first external cooling heat exchanger described above:
   internal loops or coils within a reactor stage
   external jacketing around a reactor stage
   external cooling heat exchanger (as described above) using the cooled reaction mixture on the cooling side, and combinations of 2 or more of these Various techniques can be employed to control the amount of cooling provided by the cooled stream going from the external cooling heat exchanger to the reaction stage heat exchange means. For example, the flow rate through the heat exchange means can be adjusted and/or additional amounts of similar but uncooled reaction mixture can be added to provide the desired amount of cooling.

Reactor Vessels

The design and configuration of the individual reactors is not critical to the invention and any type or combination of reactor designs will be suitable. Examples include continuously stirred tank reactor (CSTR), piston-flow (bubble) reactor, plug-flow reactor, gas-lift reactor (tube reactors), and venturi-type reactors and the like.

Reaction Stage

As known to practitioners familiar with the various types of exothermic chemical processes described below, these can be done in an extremely wide range of reactor equipment and vessel types. As will be discussed below, across the various types of exothermic chemical processes and the extremely wide range of reactor equipment and vessel types, the numbers and types of "reaction stages" can vary widely, being determined by the processes and reactions that take place and the types of general conditions, including things such as reactant(s) addition, heating, cooling and mixing. In the simplest cases, some reaction stages are the reaction vessels that have/are a single, stirred reaction mixture having essentially the same conditions and a single composition throughout (a single stage). Some vessels however have multiple stages, such stages sometimes being designated by boundaries that are differences in the conditions (e.g., reactant feed zone, cooling zone, mixing zone, etc.), physical boundary elements such as baffles and the like and/or sometimes, in plug flow situations, being without noticeable discontinuities but having a more or less continuous progression in reaction conditions over the distance the reaction mixture flows through a vessel. In any of these cases, different "reaction stages" are evidenced by differences in the reaction mixture from other stages in terms of variations in reaction temperature, conversion of reactants to product, concentrations of reactants, subsequent reactant additions, and the like. Different reaction "stages", as used herein, will thus refer generally to any of these types of situations where the reaction conditions are measurably different in one or more of these ways. Preferably, reaction stages are demarcated in terms of reaction condition discontinuity boundaries such as mixing zones, cooling zones, and/or reactant feed zones; preferably, for example, by physical vessel divisions or division elements such as baffle(s), divider(s), separate reaction vessels, or the like.

Exothermic Hydroformylation Reactions

The exothermic hydroformylation reactions and processes cooled according to the present invention are known to those skilled in the art and not specifically essential for the practice the present invention. The resulting products are generally aldehydes and/or alcohols which are converted to a wide variety of products such as acids, esters (e.g., solvents and acrylates), and plasticizer alcohols (used to make di-octyl phthalate for example) among others.

It is also noted that that the cooling invention according to the present invention can be useful in a variety of exothermic chemical processes selected from the group consisting of, hydrogenation, isomerization, hydrocyanation, hydrosilation, carbonylations, oxidations, acetoxylations, epoxidations, hydroamination, dihydroxylation, cyclopropanation, telomerizations, carbon hydrogen bond activation, olefin metathesis, olefin dimerizations, oligomerizations, olefin polymerizations, olefin-carbon monoxide copolymerizations, butadiene dimerization and oligomerization, butadiene polymerization, Heck reaction and arene coupling reaction where cross-contamination of process fluids and/or coolant fluids must be minimized. As needed for the type of chemical reaction, the process according to the present invention can be practiced across a range of relative reaction stage volumes and reaction stage conditions provided there is still the benefit of compositional similarity/compatibility between the cooled reaction mixture stream and the stage which is being cooled. Similarly, the scale of the heat loads from the reaction stages determines specific temperatures and volumes of the cooled reaction mixture stream returned to the original reaction mixture and provided for cooling other reaction stages.

As known, hydroformylation methods generally produce aldehydes by the hydroformylation of an olefinically unsaturated organic compound with carbon monoxide and hydrogen in the presence of a rhodium-phosphorus complex catalyst and free phosphorus ligand. See for example, the basic low pressure oxo hydroformylation process of U.S. Pat. No. 3,527,809; the rhodium-catalyzed liquid recycle hydroformylation process of U.S. Pat. No. 4,148,830; and U.S. Pat. No. 4,247,486 disclosing a hydroformylation process which is directed to further modifications of the basic oxo process.

This invention is applicable to improving any conventional continuous liquid recycle or gas recycle rhodium-phosphorus complex catalyzed hydroformylation process for producing aldehydes, which process is conducted in the presence of free organic phosphorus ligand. Such hydroformylation processes (also called "oxo" processes) and the conditions thereof are well known in the art as illustrated, e.g., by the continuous liquid recycle process of U.S. Pat. No. 4,148,830, the continuous gas recycle process of U.S. Pat. No. 4,247,486, and phosphite-based processes of U.S. Pat. Nos. 4,599,206 and 4,668,651. Also included are processes such as described in U.S. Pat. Nos. 5,932,772 and 5,952,530. Such hydroformylation processes in general involve the production of aldehydes by reacting an olefinic compound with hydrogen and carbon monoxide gas in a liquid reaction medium which contains a soluble rhodium-phosphorus complex catalyst, free organophosphorus ligand and higher boiling aldehyde condensation by-products.

Of course it is to be understood that the particular manner in which the hydroformylation reaction is carried out and particular hydroformylation reaction conditions employed are not critical to the subject invention and may be varied widely and tailored to meet individual needs and produce the particular aldehyde product desired.

This invention requires that the hydroformylation process employed contains at least two or more reaction stages. As discussed above, these reaction stages may have the same or different conditions. In a preferred embodiment, the reaction mixture flows from one stage to subsequent stages, with the olefin concentration in subsequent stages being lower in each stage compared to the previous stage. In this embodiment, the amount of heat required to be removed is different in each stage. However, such differences are not critical to the subject invention, and the heat load of each stage can be the same or different. It should also be understood that the makeup of the hydroformylation media and reaction conditions in the first and subsequent reaction zones can be the same or different. Accordingly, the olefinic starting material reactants encompassed by the process of this invention can be terminally or internally unsaturated and be of straight-chain or branched-chain structure or cyclic in nature, and can also be prochiral or chiral in nature. Such olefins preferably contain from 2 to 14 carbon atoms.

Illustrative olefins include but are not limited to ethylene, propylene, 1-butene, 1-pentene, 2-butene, 2-methyl propene (isobutylene), isoamylene, 2-pentene, 2-methyl-1-butene, 2-methyl-2-butene, 1-pentene, 1-hexene, 1-tetradecene, 1-heptene, 1-octene, 2-octene (cis or trans), 2-decene (cis or trans), 1-tridecene, 2-ethyl-1-hexene, propylene dimers, propylene trimers, butadiene, isoprene, styrene, 4-methyl styrene, p-isobutylstyrene, 2-vinyl-6-methoxy-2-naphthylene, 4-ethenyl-2-fluorobiphenyl, isobutyl-4-propenylbenzene, phenyl vinyl ether, 1,4-hexadiene, 3-cyclohexyl-1-butene, 3-hexene, and the like. These are illustrative examples but are not meant to limit the applicability of the invention in any way. Of course, it is understood that mixtures of different olefinic starting materials can be employed, if desired, by the hydroformylation process of the subject invention. Among the more preferred olefins are ethylene, propylene, 1-butene, 2-butene (cis or trans), isobutene and mixtures thereof.

Likewise, any conventional rhodium-phosphorus complex catalyst can be employed and such catalysts as well as methods for their preparation are well known in the art. Such rhodium-phosphorus complex catalysts may include any rhodium-organophosphorus complex, such as the rhodium-organophosphine or rhodium-organophosphite complex hydroformylation catalysts heretofore advanced for such hydroformylation processes. Of course, mixtures of such catalysts can also be employed, if desired. Moreover, it is clear that the amount of complex catalyst present in the reaction medium of a given process need only be that minimum amount necessary to provide the rhodium metal concentration desired to be employed and which will furnish the basis for at least that catalytic amount of rhodium metal necessary to catalyze the particular hydroformylation process desired. In general, rhodium metal concentrations in the range of from about 10 ppm to about 1000 ppm by weight, calculated as free metal, should be sufficient for most hydroformylation processes. It is generally preferred to employ from about 10 to 700 ppm by weight of rhodium, and more preferably, from 25 to 500 ppm by weight of rhodium, calculated as free metal.

As noted above, the hydroformylation process of this invention is carried out in the presence of free phosphorus ligand, i.e., ligand that is not complexed with the rhodium complex catalyst employed. However, while it is generally preferred that the free phosphorus ligand be the same as the phosphorus ligand of the rhodium-phosphorus complex catalyst, such is not necessary and different ligands can be employed in a given process, if desired. Accordingly, as in the case of the rhodium-organophosphorus complex catalyst, any conventional organophosphorus ligand can be employed as the free ligand and such ligands, as well as methods for their preparation, are well known in the art. Such free phosphorus ligands may include any of the organophosphine or organophosphite ligands heretofore advanced for such hydroformylation processes. Of course, mixtures of such ligands can also be employed, if desired. Thus, the hydroformylation process of this invention may be carried out in any excess amount of free phosphorus ligand, e.g., at least 0.01 mole of free phosphorus ligand per mole of rhodium metal present in the reaction medium. The amount of free phosphorus ligand employed, in general, merely depends upon the aldehyde product desired, and the olefin and complex catalyst employed. Accordingly, amounts of free phosphorus ligand present in the reaction medium ranging from about 0.01 to about 300 or more per mole of rhodium (measured as the free metal) present should be suitable for most purposes. For example, in general, large amounts of free triarylphosphine ligand, e.g., triphenylphosphine, such as more than 50 moles or, more preferably, more than 100 moles of free ligand per mole of rhodium have preferably been employed to achieve satisfactory catalytic activity and/or catalyst stabilization, while other phosphorus ligands, e.g., alkylarylphosphines and cycloalkylarylphosphines may help provide acceptable catalyst stability and reactivity without unduly retarding the conversion rates of certain olefins to aldehydes when the amount of free ligand present in the reaction medium is as little as 1 to 100 and, more preferably, 15 to 60 moles per mole of rhodium present. In addition, other phosphorus ligands, e.g., phosphines, sulfonated phosphines, phosphites, diorganophosphites, bisphosphites, phosphoramidites, phosphonites, fluorophosphites, may help provide acceptable catalyst stability and reactivity without unduly retarding the conversion rates of certain olefins to aldehydes when the amount of free ligand present in the reaction medium is as little as 0.01 to 100 and, more preferably, 0.01 to 4 moles per mole of rhodium present.

More particularly, illustrative rhodium-phosphorus complex catalysts and illustrative free phosphorus ligands include, e.g., those disclosed in U.S. Pat. Nos. 3,527,809; 4,148,830; 4,247,486; 4,283,562; 4,400,548; 4,482,749; European Patent Applications, Publication Nos. 96,986; 96,987 and 96,988 (all published Dec. 28, 1983); PCT patent application, Publication No. WO 80/01690 (published Aug. 21, 1980) and U.S. Application Ser. Nos. 581,352, filed Feb. 17, 1984 and 685,025, filed Dec. 28, 1984. Among the more preferred ligands and complex catalysts that may be mentioned are, e.g., the triphenylphosphine ligand and rhodium-triphenylphosphine complex catalysts of U.S. Pat. Nos. 3,527,809 and 4,148,830 and 4,247,486; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the diorganophosphite ligands and rhodium-diorganophosphite complex catalysts of U.S. application Ser. Nos. 581,352 filed Feb. 17, 1984, and 685,025, filed Dec. 28, 1984 and U.S. Pat. No. 4,668,651.

As further noted above, the hydroformylation reaction is typically carried out in the presence of higher boiling aldehyde condensation by-products. It is the nature of such continuous hydroformylation reactions employable herein to produce such higher boiling aldehyde by-products (e.g., dimers, trimers and tetramers) in situ during the hydroformylation process as explained more fully, e.g., in U.S. Pat. Nos. 4,148,830 and 4,247,486. Such aldehyde by-products provide an excellent carrier for the liquid catalyst recycle process. Indeed, while one may employ, if desired, any suitable solvent at the start up of a continuous process (aldehyde compounds corresponding to the desired aldehyde products being preferred), the primary solvent will normally eventually comprise both aldehyde products and higher boiling aldehyde condensation by-products due to the nature of such continuous process. Of course, aldehyde condensation by-products can also be preformed if desired and used accordingly. It is also obvious that the amount of such higher boiling aldehyde by-products present in the reaction medium may vary over wide limits and is generally governed only by equipment constraints and the particular aldehyde product to be produced. For example, initially the hydroformylation reaction can be effected in the absence or in the presence of small amounts of higher boiling aldehyde condensation by-products as a solvent for the rhodium complex catalyst, or the reaction can be conducted in the presence of upwards of 70 weight percent, or even as much as 90 weight percent, and more of such condensation by-products, based on the total liquid reaction medium. In general, ratios of aldehyde to higher boiling aldehyde condensation by-products within the range of from about 0.5:1 to about 20:1 by weight should be sufficient for most purposes. Likewise it is to be understood that minor amounts of other conventional organic co-solvents may be present if desired.

While the hydroformylation reaction conditions may vary over wide limits, as discussed above, in general it is more preferred that the process be operated at a total gas pressure of hydrogen, carbon monoxide and olefinic unsaturated starting compound of less than about 450 pounds per square inch absolute ("psia") or 3100 kiloPascals (kPa) and more preferably less than about 350 psia (2413 kPa). The minimum total pressure of the reactants is not particularly critical and is limited mainly only by the amount of reactants necessary to obtain a desired rate of reaction. More specifically, the carbon monoxide partial pressure of the hydroformylation process of this invention is preferably from about 1 to about 120 psia (7 to 830 kPa) and, more preferably, from about 3 to about 90 psia (21 to 621 kPa), while the hydrogen partial pressure is preferably about 5 to about 160 psia (34 to 1100 kPa) and more preferably from about 10 to about 100 psia (69 to 690 kPa). In general, $H_2$:CO molar ratio of gaseous hydrogen to carbon monoxide may range from about 1:10 to 100:1 or higher, the more preferred hydrogen to carbon monoxide molar ratio being from about 1:1.4 to about 50:1.

Further, as noted above, the hydroformylation process of this invention may be conducted at a reaction temperature from about 50° C. to about 145° C. However, in general, hydroformylation reactions at reaction temperatures of about 60° C. to about 120° C. and more preferably about 65° C. to about 115° C. are preferred.

Reaction Mixture

As used herein and is apparent to those knowledgeable in this area, the term "reaction mixture", "reaction fluid" or "reaction product fluid" as it is used with regard to hydroformylation processes may include, but is not limited to, a mixture which can be gas, liquid or both comprising, as may be relevant to a particular fluid state: (a) a metal-ligand complex catalyst as described above, preferably, a metal-organophosphorus ligand complex catalyst, (b) aldehyde products and aldehyde and non-aldehyde byproducts formed in the reaction, such as saturated hydrocarbons, and/or unreacted isomerized olefins corresponding to the olefin starting materials, and/or high boiling liquid aldehyde condensation byproducts (c) optionally, free ligand, (d) optionally, unreacted reactants including unreacted olefin, hydrogen and carbon monoxide, (e) optionally, inert solvents, co-solvents or hydrocarbon additives, (f) optionally, an organic solubilizing agent for said metal-ligand complex catalyst and said optional free ligand, (g) optionally, one or more inhibiting or poisoning phosphorus byproducts formed by hydrolysis in the reaction fluid, and (h) optionally buffers or other additives such as amines to mitigate acids or other side reactions. It is to be understood that the hydroformylation reaction fluid can and normally will contain these and possibly minor amounts of other incidental components that have either been unintentionally added (e.g., feedstock impurities), deliberately added or formed in situ during the process.

It is then known by practitioners how to apply the cooling process according to the present invention to perform these various hydroformylation processes in the stage-wise process that is cooled according to the present invention.

Hydroformylation Product Recovery and Recycling Steps

The reaction mixture resulting from a hydroformylation process (also referred to as "effluent stream") is fed either continuously or intermittently to a product separation zone wherein the crude aldehyde product is recovered by conventional techniques, e.g., distillation or vaporization (U.S. Pat. No. 4,148,830), membrane (US 2008/0251456), Phase separation (U.S. Pat. Nos. 5,932,772 and 5,952,530) and organic/ aqueous catalyst system (C. W. Kohlpaintner, R. W. Fischer, B. Cornils; Applied Catalysis, A 221, 2001, pp. 219-225.). Generally, the product recovery from the hydroformylation process includes one or more recycle methods, wherein by techniques described in the art, at least the metal catalyst-containing residue from the separation is recycled back to the reaction zone as disclosed, for example, in U.S. Pat. No. 5,288,918. Preferably, the remaining concentrated catalyst is recycled as a liquid stream to the reaction zone(s). Undissolved light gases are also vented off in the product separation zone and can be returned to one of the reaction stages if desired. In refining of the crude aldehyde, it is further preferred to recycle the light gases dissolved in the crude product to a reaction stage after their removal via conventional techniques; e.g., distillation, although they too may be wasted, if desired.

Figure 4:
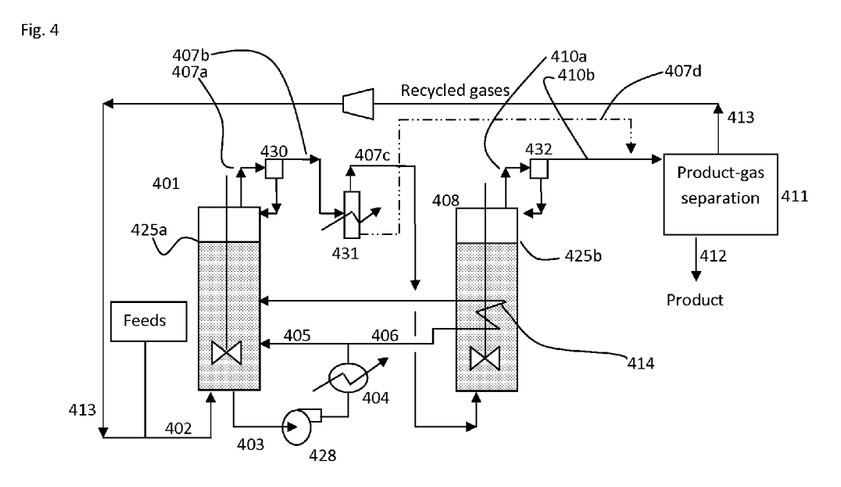
FIG. 4 is a schematic flow diagram illustrating operation of a two reactor gas recycle hydroformylation process according to the present invention.

In one embodiment of a primary gas recycle process (U.S. Pat. No. 4,593,127 and WO 2010081526) as generally shown in FIG. 4, a vent line is provided in the head space above the liquid level in the first reactor to control the internal pressure build-up in the reactor and as the means for conveying the unreacted olefin feed to a secondary reaction stage. It should be understood that the olefin starting material for the subsequent reaction stage can be taken from any gaseous stream which could be vented from the first reaction stage as off-gas. While such olefin starting material for the subsequent reaction stage can be derived from any appropriate gas vent containing unreacted olefin and incidental alkane by-products taken from any suitable location in the first reaction stage, it is preferred to employ the vent stream from either the reactor headspace and/or from the product separation step as the feed for the subsequent rhodium-catalyzed hydroformylation process. In the subsequent reaction stage, olefin-containing vented gas from the first reaction stage is admixed with make-up synthesis gas and the resulting feed is introduced into the reaction stage of the subsequent system which contains a catalyst system which may be the same or different than the first reaction system. It should be understood that in a process wherein only gas stream transfers from one reaction stage to the next (as is the case here), the term "process stream" refers to gaseous material flow.

Hydroformylation Process Diagrams

Figure 1:
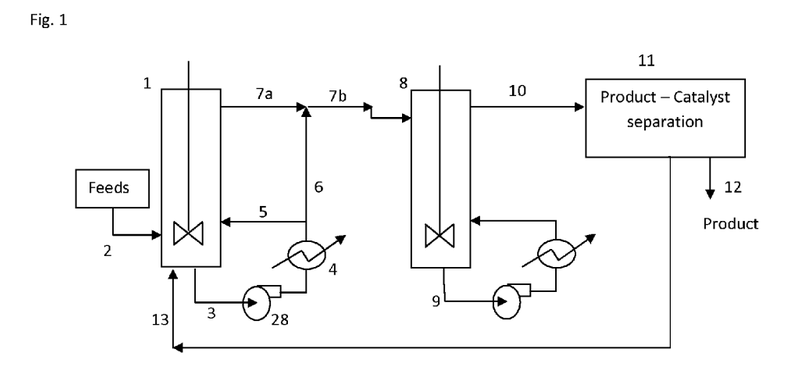
FIG. 1 is a schematic flow diagram of a generalized two stage process which is representative of the prior art.

Referring to FIG. 1, in a simplified diagram of a conventionally cooled, prior art hydroformylation process, agitated reactor 1 having a single reaction stage and containing a reaction mixture is supplied with reactants (olefin and synthesis gas) and optionally catalyst in feed stream 2. A stream 13 containing recycle components including recycled catalyst is returned and also added to the reactor. A pump 28 or other means is used to remove a reaction mixture stream 3 from the reactor and deliver it to an external cooling heat exchanger 4. The heat exchanger cools the reaction mixture. Cooled reaction mixture stream 5 is returned to the reaction stage. The reactants added near the bottom of the reactor form a reaction mixture and provide a product-containing reaction mixture upwardly through the reactor and provide a product-containing "transfer stream" of reaction mixture 7a, out of the reactor for transfer via 7b to subsequent reactor 8.

In another alternative conventional embodiment which can be seen in FIG. 1, instead of transfer stream 7a (which can be omitted), cooled transfer stream 6 from the heat exchanger 4 is delivered directly into the reaction mixture in subsequent reactor 8 via reaction mixture transfer stream 7b.

In such conventional hydroformylation process subsequent agitated reactor 8 employs its own individual external cooling heat exchanger which is supplied through stream 9 and returned to the reactor 8. A transfer stream of reaction mixture 10 is removed from the reactor 8 and provided to a product and catalyst separation and recovery unit operation 11 which provides product 12 and recycled components in stream 13.

Figure 2:
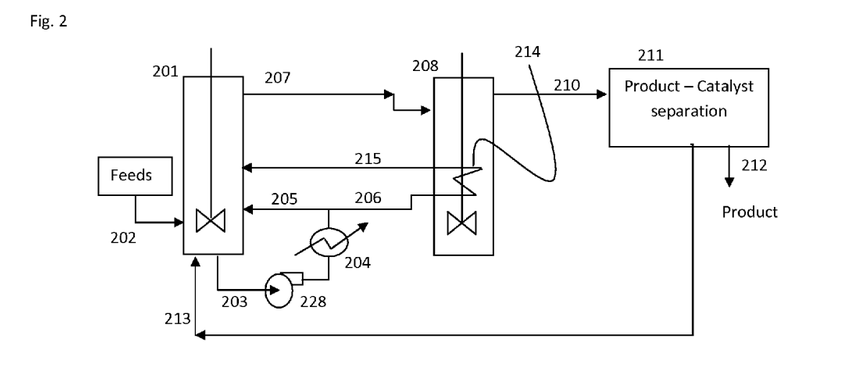
FIG. 2 is a schematic flow diagram illustrating operation of a two reactor liquid recycle hydroformylation process according to present invention wherein cooled reaction mixture from the heat exchanger for the first reactor is also used in a cooling coil in the second reactor.

Referring to FIG. 2, in a simplified diagram of a cooled hydroformylation process according to the present invention, an agitated reactor 201 having a single reaction stage and containing a reaction mixture is supplied with reactants (olefin and synthesis gas) and optionally catalyst in feed stream 202. A stream 213 containing recycle components including recycled catalyst is returned and also added to the reactor. A pump 228 or other means is used to remove a reaction mixture stream 203 from the reactor and deliver it to an external cooling heat exchanger 204. The heat exchanger cools the reaction mixture and therein or shortly thereafter the reaction mixture stream is divided into cooled reaction mixture streams 205 and 206. Cooled reaction mixture stream 205 is returned to the reaction stage. Cooled reaction mixture stream 206 is provided to heat exchange means 214 (using either pressure or optionally an additional pump) and used to cool the reaction mixture and subsequent reactor 208. The heat exchange means shown in FIG. 2 represents an internal loop or coil type of the exchange means but can also be a jacket type heat exchanger or an external cooling heat exchanger (or both) that then provides cooling of the reactor 208 reaction mixture. After use of the cooled reaction mixture stream 206 in the heat exchange means 214, it is returned in stream 215 to the reaction mixture in reactor 201.

The reactants stream 202 and recycle stream 213 added near the bottom to the reaction mixture in reactor 201 (or other means) provide a product-containing reaction mixture upwardly through the reactor and a product-containing transfer stream of reaction mixture 207, out of the reactor for transfer to subsequent reactor 208. In another alternative conventional embodiment, not shown in FIG. 2, instead of transfer stream 207 (which can be omitted), a third cooled transfer stream from the heat exchanger 204 is delivered directly into the reaction mixture in subsequent reactor. A transfer stream of reaction mixture 210 is removed from the reactor 208 and provided to a product and catalyst separation and recovery unit operation 211 which provides product 212 and recycled components in stream 213.

Figure 3:
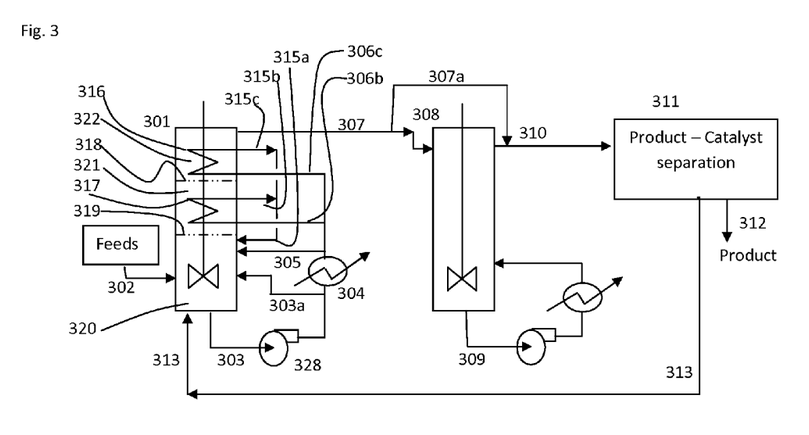
FIG. 3 is a schematic flow diagram illustrating operation of a hydroformylation process according to the present invention where the first reactor vessel has three reaction stages separated by baffles.

Referring to FIG. 3, in a simplified diagram of another cooled hydroformylation process according to the present invention, an agitated reactor vessel 301 has three separate reaction stages, separated by baffles 318 and 319 and each reaction stage containing a different reaction mixture. Initial reaction stage 320 containing a reaction mixture receives reactants (olefin and synthesis gas) and optionally catalyst in feed stream 302. A stream 313 containing recycle components including recycled catalyst is returned and also added to the reactor.

The reactants/catalyst stream 302 and recycle stream 313 added to the reaction mixture in reaction stage 320 provide a product-containing reaction mixture upwardly through the reactor to subsequent reactor stage 321 and similarly from there to subsequent reactor stage 322 and subsequently from there, a product-containing transfer stream of reaction mixture 307, out of the reactor 301 for transfer to an optional subsequent reactor 308 or, alternatively, directly via 307a to the product-catalyst separation system 311.

Referring to reactor 301 in FIG. 3, from reaction stage 320, a pump 328 or other means is used to remove a reaction mixture stream 303 from the reactor and deliver it to an external cooling heat exchanger 304. Optionally some of the reaction mixture in optional stream 303a is returned to reaction stage 320 without being cooled in stream 303a depending upon cooling needs and requirements of the pumping means being used. The heat exchanger 304 cools the reaction mixture and therein or shortly thereafter the reaction mixture stream is divided into cooled reaction mixture streams 305, 306b, and 306c. Cooled reaction mixture stream 305 is returned to the reaction stage 320. Cooled reaction mixture stream 306b is provided to heat exchange means and used to cool the reaction mixture in reaction stage 321. Cooled reaction mixture stream 306c is provided to heat exchange means used to cool the reaction mixture in reaction stage 322. The heat exchange means shown in reaction stages 321 and 322 represent internal loop or coil type of the exchange means but can also be a jacket type heat exchanger or an external cooling heat exchanger that then provides cooling of the 321 and 322 reaction stages. After use of the cooled reaction mixture streams 306b and 306c in their respective heat exchange means they are returned in streams 315b and 315c to the reaction mixture in reaction stage 320.

A transfer stream of reaction mixture 310 is provided to a product and catalyst separation and recovery unit operation 311 which provides product 312 and recycled components in stream 313.

Referring to FIG. 4, in a simplified diagram of another cooled hydroformylation process according to the present invention using a gas recycle process, an agitated reactor 401 having a single reaction stage and containing a reaction mixture is supplied with reactants (olefin and synthesis gas) and optionally catalyst in feed stream 402. A stream 413 containing recycle components including recycled gases is returned (optionally via a compressor) and also added to the reactor. A pump 428 or other means is used to remove a reaction mixture stream 403 from the reactor and deliver it to an external cooling heat exchanger 404. The heat exchanger cools the reaction mixture and therein or shortly thereafter the reaction mixture stream is divided into cooled reaction mixture streams 405 and 406. Cooled reaction mixture stream 405 is returned to the reaction mixture in reactor 401. Cooled reaction mixture stream 406 is provided to heat exchange means 414 and used to cool the reaction mixture and subsequent reactor 408. The heat exchange means shown in FIG. 4 represents an internal loop or coil type of the exchange means but can also be a jacket type heat exchanger or an external cooling heat exchanger that then provides cooling of the reactor 408 reaction mixture. After use of the cooled reaction mixture stream 406 in the heat exchange means 414, it is returned in stream 415 to the reaction mixture in reactor 201.

The reactants stream 402 and recycle stream 413 added near the bottom to the reaction mixture in reactor 401 provide a product-containing gaseous mixture upwardly through the reactor and a product-containing gaseous product mixture "transfer stream" 407a, out of the reactor and into a demister 430. The catalyst-containing process fluid liquid level is maintained at a set point 425a. In the demister any entrained catalyst or process fluid is removed and returned to the reactor 401 and the gaseous product stream (with unreacted reactants such as synthesis gas, olefins, alkanes, and inert gases) is moved by stream 407b going to an optional gas-liquid separation unit 431 wherein the crude product may be condensed from the cooled gaseous stream. The condensed crude product stream 407d is then sent on to further processing and the uncondensed gases are transferred by 407c to the next reaction stage 408. The catalyst-containing process fluid liquid level is maintained at a set point 425b. A gaseous product mixture is removed from the top of 408 via transfer stream 410a and provided into a demister 432. In the demister, any entrained catalyst or process fluid is removed and returned to 408 and the gaseous crude product mixture 410b (combined with optional stream 407d) is sent to product-gas separation and recovery unit operation 411 which provides product 412 and recycled gaseous components in stream 413.

In all cases, the crude products are then sent to refining and other conventional operations to obtain the final products such as alcohols, aldol-derivatives, acids, esters, and the like.

EXPERIMENT

The following experiment serve to illustrate the practice of this invention and not to limit it.

The feed streams of ethylene, synthesis gas (also referred to as "syn gas", comprising hydrogen, carbon dioxide, carbon monoxide, water vapor and methane) and a rhodium phosphine-type catalyst were supplied to a hydroformylation reactor having the design as generally shown in FIG. 3 having 3 reaction stages separated by baffles, as shown. The feed rates were:

Ethylene—approximately 3.8 gram moles ethylene per liter per hour (gmole/L/hr)

Syngas—approximately 4.2 gmole/L/hr of syn gas (approximately 1:1 $CO:H_2$ mole ratio), and Catalyst—approximately 122 gms/L/hr of catalyst (from stream 313).

The unit "gmole/L/Hr" refers to the moles (in grams) divided by the total number of liters of reaction fluid in the system divided by the number of hours. The unit "gms/L/Hr" refers to the mass (in grams) divided by the total number of liters of reaction fluid in the system divided by the number of hours. The heat of reaction was removed and the temperatures of the three stages were controlled in the following manner.

A reaction mixture flow of approximately 22,700 gms/L/hr was removed from reaction stage 320 of the reactor in stream 303. Of this stream, a stream 303a of 15,200 gms/L/hr bypassed the cooler and was either returned to the bottom reactor stage 320 in order to meet the minimum flow requirements of the removal pump or combined with the cooled reaction mixture stream(s) to adjust their temperatures as needed for individual reaction stage temperature control.

The remaining 7,500 gms/L/hr of heat exchange reaction mixture was passed through the cooler and cooled to approximately 30° C. Then, 3,400 gms/L/hr of this cooled reaction mixture (stream 305) was fed back to the reaction stage 320 that it was removed from to provide cooling.

Also from the cooled reaction mixture stream, 2,900 gms/L/hr of cooled reaction mixture (stream 306b) was mixed with a variable portion of uncooled catalyst (not shown) and provided into and through the internal heat exchange coils of the middle (2nd) reaction stage 321 of the reactor, and returned to stage 320 of the reactor. The temperature of the reaction mixture fed to the 2nd stage cooling coils increased in temperature from 79.0° C. to 84.1° C. as it passed through the coil.

Also from the cooled reaction mixture stream, 1,200 gms/L/hr of cooled reaction mixture (stream 306c) was mixed with a variable portion of uncooled catalyst (not shown), provided into and passed through the internal heat exchange coils in the top (3rd) reaction stage 322 of the reactor and returned to stage 320 of the reactor. The temperature of the reaction mixture fed to the 3rd stage cooling coils increased in temperature from 85.4° C. to 86.1° C. as it passed through the coil.

The bottom reaction stage 320 temperature was thereby controlled at or near the desired temperature of 91.0° C.; the middle reaction stage was thereby controlled at or near the desired temperature of 90.0° C.; and the third (top) reaction stage temperature was thereby controlled at or near the desired temperature of 88.0° C.

The invention claimed is:

1. An improved exothermic hydroformylation process having at least two reaction stages, comprising the following steps:
    (a) reacting hydroformylation reactants exothermically in a first reaction stage in a fluid reaction mixture to form a reaction product;
    (b) transferring a process stream of fluid reaction mixture from a reaction stage to one or more later and separate reaction stages(s) for further exothermic, product-forming reaction and then to product recovery unit operation(s);
    (c) transferring a heat transfer stream of reaction mixture from a reaction stage to an external heat exchanger where it is cooled and dividing the cooled stream into multiple cooled reaction mixture streams;
    (d) transferring a cooled reaction mixture stream from step (c) back into the same reaction stage from which it was removed to cool the reaction mixture in that reaction stage;
    (e) transferring at least one cooled reaction mixture stream(s) from step (c) into and through heat exchange means that cool a different reaction stage, and returning it to the same reaction stage from which removed; and
    (f) separating and recovering a reaction product from the reaction mixture and optionally recycling at least some reaction mixture components to the reaction mixture in a reaction stage.

2. An improved hydroformylation process according to claim 1 comprising at least two reaction stages that are in separate reactor vessels.

3. An improved hydroformylation process according to claim 1 comprising at least two reaction stages that are in the same reactor vessel and separated by baffles.

4. An improved hydroformylation process according to claim 2 wherein at least two different rhodium-containing hydroformylation catalysts are employed and are employed in different reaction stages.

5. An improved hydroformylation process according to claim 1 comprising recycling catalyst from step (f) back to the reaction mixture in a reaction stage.

6. An improved hydroformylation process according to claim 2 for producing an aldehyde or a mixture of aldehydes and having at least first and second separate reaction stages, comprising the following steps:
    (a) reacting hydroformylation reactants comprising an olefin, hydrogen and carbon monoxide exothermically in a liquid reaction mixture in a first reaction stage using a rhodium-containing hydroformylation catalyst to give an aldehyde or a mixture of aldehydes having one more carbon atom than the starting olefin;
    (b) transferring a process stream of reaction mixture from the first reaction stage to the second reaction stages for further exothermic conversion of reactants into aldehyde product;
    (c) transferring a heat transfer stream of reaction mixture from the first reaction stage to an external cooling heat exchanger where it is cooled and dividing the cooled stream into two cooled reaction mixture streams;
    (d) transferring the first cooled reaction mixture stream from step (c) back into the first reaction stage from which it was removed to cool the reaction mixture in that reaction stage; and
    (e) transferring the second cooled reaction mixture stream from step (c) into and through heat exchange means that cools the second reaction stage, and returning it to the first reaction stage.

7. An improved hydroformylation process according to claim 6 using a rhodium-phosphorus complex catalyst and free phosphorus ligand.

8. An improved hydroformylation process according to claim 6 comprising using a gas recycle process wherein a product-containing gaseous product mixture is transferred out of a reaction stage to a catalyst removal means, from which catalyst removal means (a) catalyst is returned to the reaction stage and (b) the gaseous product reaction mixture stream (with unreacted reactants) is transferred to the second reaction stages(s) for further exothermic conversion of reactants into aldehyde product and a recycle stream containing gases is returned to the reaction mixture.

9. An improved hydroformylation process according to claim 6 comprising using two agitated reactors, each having a single reaction stage.

10. An improved hydroformylation process according to claim 6 comprising using an agitated reactor vessel with at least two separate reaction stages separated by baffles wherein a stream of cooled reaction mixture from the external cooling heat exchanger is returned to the first reaction stage and streams of cooled reaction mixture from the external cooling heat exchanger are provided to heat exchange means for the other reaction stage(s), used to cool the reaction mixtures in those stages and then returned to the reaction mixture in the first reaction stage.

11. An improved hydroformylation process according to claim 6 comprising using two agitated reactor vessels, the first having a single reaction stage, and the second having 2 or more reaction stages separated by baffles, wherein the cooled reaction mixture stream from the external cooling heat exchanger is divided into multiple cooled reaction mixture streams with one cooled stream returned to the first reaction stage and the remainder of the cooled streams provided to some or all of the heat exchange means in the second reactor.

12. An improved hydroformylation process according to claim 1 wherein the olefin is selected from ethylene, propylene, 1-butene, 2-butene (cis or trans), isobutene and mixtures thereof.

13. An improved hydroformylation process according to claim 12 wherein the olefin is ethylene or propylene.

14. An improved hydroformylation process according to claim 1 wherein uncooled reaction mixture is added to the cooled reaction mixture from the external cooling heat exchanger to achieve a desired temperature in the cooled reaction mixture stream provided to the heat exchange means that cools a subsequent reaction stage.

15. An improved hydroformylation process according to claim 1 wherein the cooled mixture stream from the external cooling heat exchanger is provided to internal coil heat exchange means in the subsequent reaction stage(s).

* * * * *